(12) United States Patent
Tanielyan et al.

(10) Patent No.: US 7,351,867 B2
(45) Date of Patent: Apr. 1, 2008

(54) CATALYST SYSTEM FOR AEROBIC OXIDATION OF PRIMARY AND SECONDARY ALCOHOLS

(75) Inventors: Setrak K. Tanielyan, Maplewood, NJ (US); Robert L. Augustine, Livingston, NJ (US); Indra Prakash, Alpharetta, GA (US); Kenneth E. Furlong, Evans, GA (US); Handley E. Jackson, North Augusta, SC (US)

(73) Assignee: The NutraSweet Company, Chicago, IL (US)

( * ) Notice: Subject to any disclaimer, the term of this patent is extended or adjusted under 35 U.S.C. 154(b) by 0 days.

(21) Appl. No.: 11/065,222

(22) Filed: Feb. 24, 2005

(65) Prior Publication Data

US 2007/0078284 A1 Apr. 5, 2007

Related U.S. Application Data

(60) Provisional application No. 60/547,837, filed on Feb. 26, 2004.

(51) Int. Cl.
*C07C 45/00* (2006.01)

(52) U.S. Cl. ............... 568/320; 568/391; 568/472

(58) Field of Classification Search ............... None
See application file for complete search history.

(56) References Cited

U.S. PATENT DOCUMENTS 5,856,584 A * 1/1999 Prakash et al. ............ 568/449
5,973,209 A * 10/1999 Prakash et al. ............ 568/483
6,825,384 B1 * 11/2004 Prakash et al. ............ 568/402

OTHER PUBLICATIONS

Anelli et al. Fast and Selective Oxidation of Primary Alcohols to Aldehydes or to Carboxylic Acids and of Secondary Alcohols to Ketones Mediated by Oxoammonium Salts under Two-Phase Conditions. Journal of Organic Chemistry, 1987, vol. 52, pp. 2559-2562.*

Anelli et al. Oxidation of Diols with Alkali Hypochlorites Catalyzed by Oxammonium Salts under Two Phase Conditions.☐☐Journal of Organic Chemistry, 1989, vol. 54, pp. 2970-2972.*

Gamez et al. Copper (II)-Catalyzed aerobic oxidation of primary alcohols to aldehydes.☐☐Chemical Communications, 2003, pp. 2414-2415.*

* cited by examiner

*Primary Examiner*—Sikarl A. Witherspoon
(74) *Attorney, Agent, or Firm*—Jeffrey M Hoster

(57) ABSTRACT

The present invention relates to a process of oxidation of alcohols selectively to aldehydes or ketones with molecular oxygen using a TEMPO based catalyst, Fe-bipyridyl or Fe-phenantroline co-catalyst and N-bromosuccinimide promoter in acetic acid solvent. The oxidation takes places at high rates and high aldehyde selectivity at temperatures in the range 45-50° C. and oxygen or air pressures of 0-15 psi. The alcohol conversion of 95-100% and aldehyde selectivity higher than 95% are achieved over 3-4 hours reaction time. Aldehydes such as 3,3-dimethyl-1-butanal can be produced efficiently using the present invention.

28 Claims, 1 Drawing Sheet

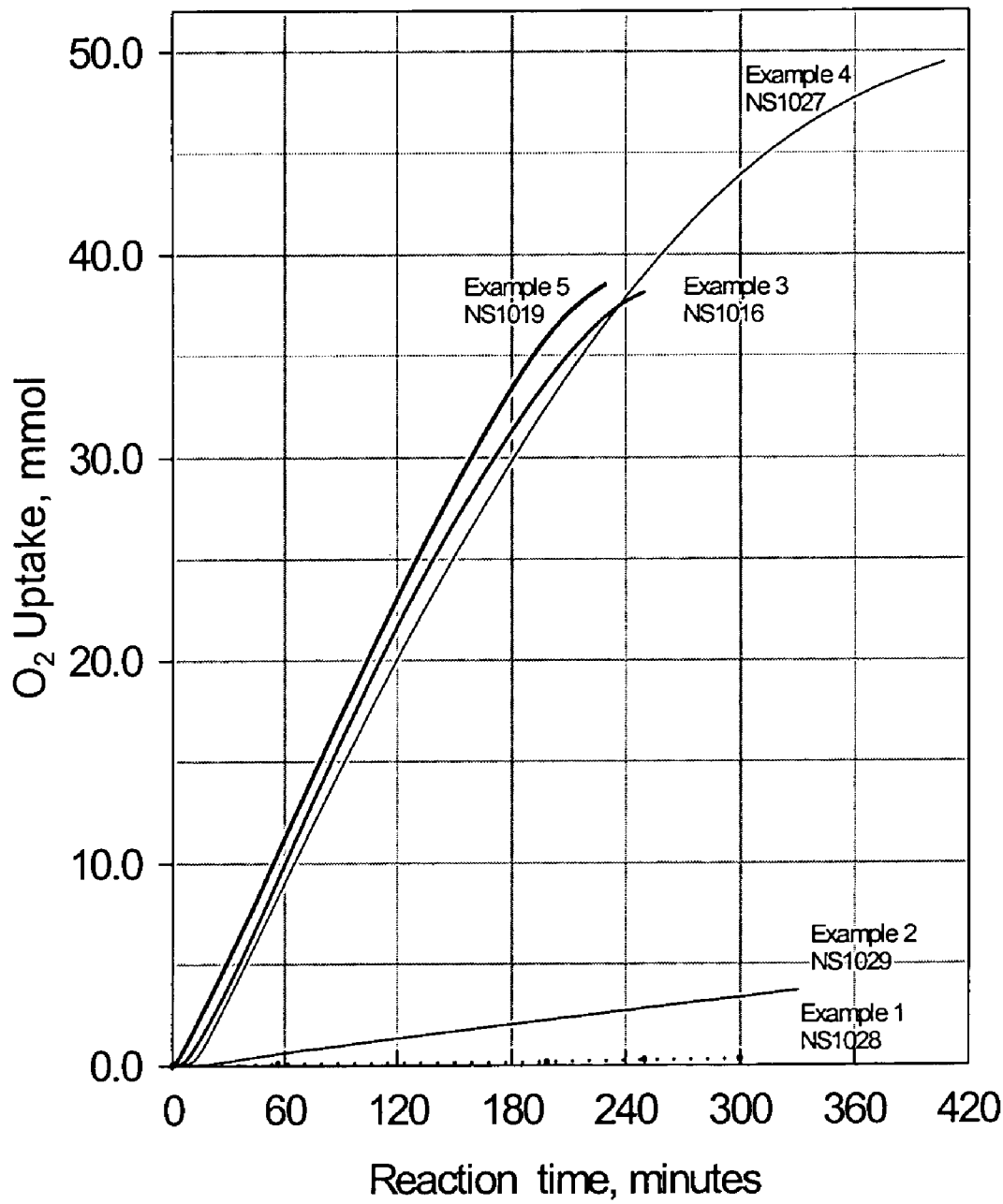
Fig 01. Oxidation of 3,3-dimethyl-1-butanol
High alcohol load at 7cc $CH_3COOH$
Comparative example
TEMPO = 0.536mmol, [$MeN_x$] 0.416mmol
Temperature 45°C, Stirring Rate 1500RPM

CATALYST SYSTEM FOR AEROBIC OXIDATION OF PRIMARY AND SECONDARY ALCOHOLS

This application claims the priority of U.S. Provisional Application No. 60/547,837, filed on Feb. 26, 2004.

FIELD OF THE INVENTION

The present invention relates to catalyst system which exhibits high activity and selectivity in the oxidation of alcohols to aldehydes or acids using molecular oxygen as a terminal oxidant. More specifically, the invention relates to a catalyst system which comprises a synergistic mixture of 2,2,6,6, -tetramethylpiperidinyloxy catalyst (hereinafter referred to as "TEMPO" or "TEMPO catalyst"), Iron-Bipyridyl complex (hereinafter referred to as co-catalyst (CC)) and N-Bromosuccinimide (referred to as bromine promoter). Such a synergistic couple is particularly useful for, but not limited to, oxidation of primary, secondary aliphatic and aromatic alcohols.

BACKGROUND OF THE INVENTION

The catalytic oxidation of alcohols selectively to carbonyl compounds is essential for many important transformations in the synthetic organic chemistry. A large number of oxidants have been reported in the literature and most of them are based on transition metal oxides such as chromium and manganese (S. Kirk-Othmer Mitchell, Enciclopedia of Chemical Technology, $4^{th}$ ed., Wiley-Interscience, New York, Vol. 2, p 481, (1992); Hudlicky, M. "Oxidations in Organic Chemistry", ACS Monograph No. 186 American Chemical Society Washington D.C. (1990); Sheldon R. A., Kochi J. K. Metal Catalized Oxidation of Organic Compounds. New York, Academic Press, 1981; Ley, S. V., Madin, A. In comprehensive Organic Synthesis, Trost B., Fleming, I., Eds.; Pergamon Oxford, 1991; Vol 7, p 251; Mijs, W. J., DeJonge, C. R. H. I. Organic Synthesis by Oxidation with Metal Compounds; Plenum: New York, 1968). The methods described require the use of stoichiometric amounts of inorganic oxidants, generally highly toxic chromium or manganese compounds, which creates serious problems related to their handling and disposal.

A particularly convenient procedure for the oxidation of primary and secondary alcohols is reported by Anelli and co-workers (J. Organic Chemistry, 1987, 52, 2559; J. Organic Chemistry, 1989, 54, 2970). The oxidation has been carried out in a two-phase system ($CH_2Cl_2$-water) utilizing the TEMPO as a catalyst and cheap and readily accessible NaOCl as an oxidant. The co-catalyst KLBr enhances the reaction rate and the aqueous phase is buffered at pH 8.5-9.5 using $NaHCO_3$. The use of a quaternary ammonium salt as a phase transfer catalyst furthers the oxidation of alcohols to carboxylic acids. The same procedure was modified by using $NaClO_2$ as the oxidant in the presence of catalytic amounts of TEMPO and NaOCl. This led to the formation of the carboxylic acid as the main product (U.S. Pat. No. 6,127, 573).

Prakash et al. in U.S. Pat. No. 5,856,584 report a similar procedure for oxidation of 3,3-Dimethyl-1-butanol. According to this procedure the 3,3-Dimethyl-1-butanol is oxidized to 3,3-dimethyl-1-butanal with NaOCl in a two-phase system using $CH_2Cl_2$ as a reaction solvent. The stable 2,2,6,6-tetramethyl-1-piperidinyloxy free radical and a KBr are used as an efficient catalytic system to produce the desired aldehyde in 80% isolated yield.

A particularly efficient method for oxidation of primary and secondary alcohols was also reported in U.S. application Ser. No. 60/443,749. The oxidation is carried out at temperature -5-0° C. using the TEMPO as a catalyst, $Na_2B_4O_7$ as a co-catalyst and NaOCl as an oxidant. The procedure does not require reaction solvent and is carried out without KBr promoter. The aqueous phase is buffered at pH 8.7-9.2 using $NaHCO_3$. This procedure gives small amount of chlorinated hydrocarbon impurities.

The search for efficient, easily accessible catalysts and "clean" oxidants such as hydrogen peroxide, hydroperoxides or molecular oxygen for industrial applications is still a challenge (Dijksman, A., Arends I. W. C. E. and Sheldon R., Chem. Commun., 1999, 1591-1592; Marko I. E., P. R. Giles, Tsukazaki M., Brown S. M. and Urch C. J., Science, 19696, 274, 2044). A large number of transition metal complexes and oxidants have been reported to catalyze the selective oxidation of primary alcohols to aldehydes with varying levels of effectiveness such as $RuCl_3$-$NaBrO_3$ (Konemoto S., Tomoioka S., Oshima K.), Bull. Chem. Soc. Japan. 1986. V. 59. N1, P. 105), $Bu_4NRuO_4$-4-Methylmorpholine N-oxide (Griffith W. P., Ley S. V., Whitcombe G. P., White A. D)., Chem. Commun. 1987, N21, p. 1625), $H_2O_2$ and tert-Butylhydroperoxide (t-BuOOH) (Y. Tsuji, T. Ohta, T. Ido et al.), J. Organometallic Chemistry, 270, 333 (1984), (T. M. Jiang, J. C. Hwang, H. O. Ho, C. Y. Chen), J. Chin. Chem. Soc., 35, 135, (1988). The methods described have only limited use since the overall yields are low and some of them require the application of precious metal complexes or expensive primary oxidants.

In the area of the aerobic oxidation of alcohols, very few efficient systems are currently available. A catalyst system based on TEMPO and $Mn(NO_3)_2$—$Co(NO_3)_2$ or $Mn(NO_3)_2$—$Cu(NO_3)_2$ was recently reported (A. Cecchetto, F. Fontana, F. Minisci and F. Recupero) Tetrahedron Letters, 42, 6651-6653 (2001). The oxidation requires diluted solutions of the starting alcohol in acetic acid solvent (in the range 6-10% v/v) and takes place at ambient temperatures and at atmospheric pressure of oxygen. A serious drawback of the method is the rapid deactivation of the catalyst at higher alcohol concentrations, resulting in the catalyst system being virtually inactive Because of this, direct commercial application is not economically feasible as higher alcohol concentrations are typically required in such processes.

Despite the extensive work reported in the area of the selective oxidation of primary alcohols there is still a continuous need for developing highly efficient and economical oxidation methods using molecular oxygen as environmentally friendly oxidants. It is the object of the present invention to provide such an oxidation method.

SUMMARY OF THE INVENTION

The process according to this invention comprises oxidizing primary and secondary alcohols with molecular oxygen in the presence of a catalyst system, which comprises a synergistic mixture of TEMPO catalyst (represented by formula I or II), Iron-bipyridyl complex co-catalyst (shown in formula III) and N-bromosuccinimide promoter (structure IV).

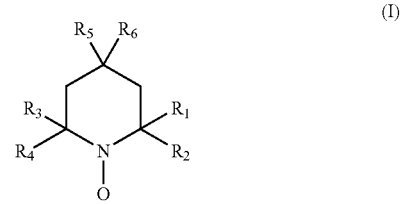

(I)

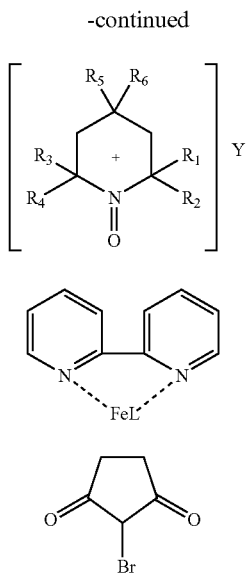

(II)

(III)

(IV)

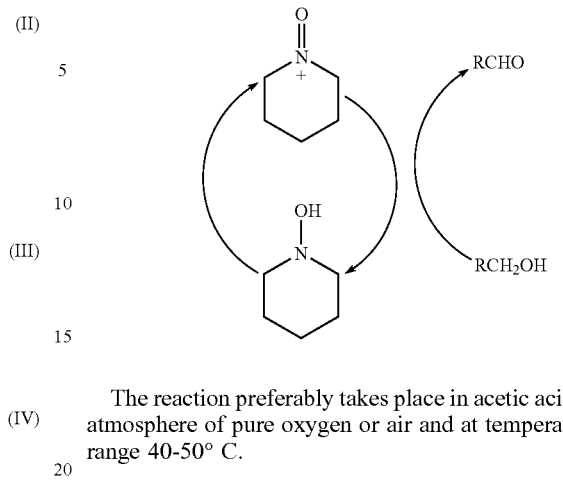

In Formulas (I) and (II), $R_1$, $R_2$, $R_3$ and $R_4$ independently are lower alkyl or substituted alkyl groups of the same or different structures. $R_5$ and $R_6$ are hydrogen, alkyl or lower alkoxy or one is hydrogen and the other is lower alkoxy, hydroxy, amino, alkyl or dialkylamino, alkylcarbonyloxy, alkylcarbonylamino, or $R_5$ and $R_6$ are ketal. The $Y^-$ group is an anion.

The co-catalyst according to the invention is a metal ligand complex, where the metal is chosen from groups IB, IVA, Va, VIA, VIIA or VIII of the Periodic Table of Elements and the ligand could be 2,2'-dipyridyl, 1,10-phenantroline, 2,2'-dipyridylamine, 3,6-di-2-pyridyl-1,2,4,5-tetrazine, di-2-pyridylketone, tetra-2-pyridinylpyrazine or 2,2':6'2"-terpyridine.

The bromine promoter according to the invention is N-bromosuccinimide, N-bromophthalimide, bromine, HBr or inorganic bromide such as NaBr, KBr or LiBr.

The TEMPO/co-catalyst/bromine promoter catalyzed oxidation is described by the reaction shown in Scheme 1. According to this, the oxidation takes place via a cascade mechanism in which a number of oxidizing species exist in a dynamic equilibrium. While not wishing to be bound by theory, it is believed that the molecular oxygen oxidizes the co-catalyst ($Fe^{2+}$-bipyridyl complex) to its oxidized form ($Fe^{3+}$-bipyridyl). The $Br^-$ is then oxidized to $BrO^-$, which converts the reduced form of the TEMPO into the oxonium form. It is believed that the oxonium form selectively oxidizes the alcohol function to aldehyde.

Scheme 1

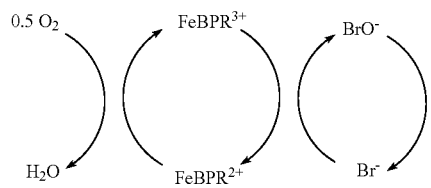

The reaction preferably takes place in acetic acid media in atmosphere of pure oxygen or air and at temperature in the range 40-50° C.

DETAILED DESCRIPTION OF THE FIGURE

FIG. 1 shows graphical representations of the oxygen uptake of the reactions in Comparative Examples 1 and 2 as well as Examples 3-5.

DETAILED DESCRIPTION OF THE INVENTION

The inventive process comprises oxidizing primary and secondary alcohols with molecular oxygen in the presence of a catalyst system. The catalyst system comprises a synergistic mixture of TEMPO catalyst (represented by formula I or II), Iron-bipyridyl complex co-catalyst (shown in formula III) and N-bromosuccinimide promoter (structure IV).

The term primary or secondary alcohols as used in the present invention describe organic compounds having primary or secondary hydroxyl groups. The term lower alcohol as used herein refers to alcohols having 1 to 10 carbon atoms while the term higher as used herein refers to alcohols having 11 or more carbon atoms. Examples of primary and secondary alcohols thereof include alcohols such as methanol, ethanol, n- and isopropyl alcohol, n-, iso- and sec-butyl alcohol, pentyl alcohol, hexyl alcohol, neopentyl alcohol, neohexyl alcohol, heptyl alcohol, octyl alcohol, lauryl alcohol, tridecyl alcohol, myristyl alcohol, nonadecyl alcohol, eicosyl alcohol. Examples of unsaturated alcohols include 3-methyl-3-buten-1-ol, allyl alcohol, crotyl alcohol and propargyl alcohol. Examples of aromatic alcohols include benzyl alcohol, phenyl ethanol, phenyl propanol and the like. The term TEMPO based catalyst as used herein refers to compounds of formula I or II above. Here, $R_1$, $R_2$, $R_3$ and $R_4$ independently are lower alkyl or substituted alkyl groups of the same or different structures. $R_5$ and $R_6$ are both hydrogens, alkyl or are lower alkoxy or one is hydrogen and the other is lower alkoxy, hydroxy, amino, alkyl or dialkylamino, alkylcarbonyloxy, alkylcarbonylamino, or can jointly be an oxygen or ketal. The $Y^-$ group is an anion. The term "lower alkyl" means straight chain or branched saturated hydrocarbon groups with up to 8 carbon atoms, such as methyl, ethyl, n-propyl, isopropyl, isobutyl, pentyl, n-hexyl and the like. The term "lower alkoxy" means alkyl groups bonded via an oxygen atom, such as methoxy, ethoxy and the like. The term "lower alkylcarbonyloxy" means lower alkylcarbonyl group bonded via an oxygen atom. The term "lower alkylcarbonyl" means lower alkyl groups bonded via carbonyl group and is represented by groups such as acetyl, propionyl and the like. The term "lower carbonylamino" means lower alkylcarbonyl group bonded via nitrogen atom such as acetylamino and the like.

Examples of TEMPO based compounds contemplated for use in the present invention include, but are not limited to 2,2,6,6, -tetramethylpiperidine N-oxyl (TEMPO) and the 4-substituted derivatives thereof including 4-methoxy-TEMPO, 4-ethoxy-TEMPO, 4-acetoxy-TEMPO, 4-acetamino-TEMPO, 4-hydroxy-TEMPO, 4-benzoyloxy-TEMPO, 4-amino-TEMPO, N,N-dimethyalamino-TEMPO, 4-oxo-TEMPO and the polymeric versions of TEMPO such as poly [(6-[1,1,3,3-tetramethylbutyl)amino]-s-triazine-2,4-diyl], [(2,2,6,6-tetramethyl-4-piperidyl)imino]hexamethylene[(2,2,6,6-tetramethyl-4-piperidinyl)imino]], known also as Chimasorb 944. The immobilized forms of any of the above-described compounds can also be used. As a solid support one can use materials such as polymers, composites, carbon materials, or inorganic carriers such as aluminum oxide or titanium oxide. The immobilization of the TEMPO catalyst can be accomplished, for example, by physical adsorption on the surface or via tethering through organic or inorganic linkers The co-catalyst according to the invention is selected from the group comprising metal salts and metal-ligand complexes, which contain at least one metal atom or ion from the groups IB, IVA, VA, VIA, VIIA or VIII of the Periodic Table of Elements.

Suitable metal cations that can be employed in the present invention include, but are not limited to: $Fe^{2+}$, $Fe^{3+}$, $Cu^{2+}$, $Mn^{2+}$, $Mn^{3+}$, $Co^{2+}$, $Co^{3+}$. The anionic species used in forming the salts may be nitrates, bromides, chlorides, phosphates, sulfates, acetates, acetylacetonates and the like. The salts can be used individually or in any combination of two or more metal species. The metal salt or salts can also be used in a complex form with ligands such as 2,2'-dipyridyl, 1,10-phenantroline, 2,2'-dipyridylamine, 3,6-di-2-pyridyl-1,2,4,5-tetrazine, di-2-pyridylketone, tetra-2-pyridinylpyrazine or 2,2':6'2"-terpyridine, ethylenediaminetetraacetic acid or disodium salt, 8-hydroxyquinoline, or phthalocyanine. The metal-ligand complex could be prepared in situ (or during the reaction) or could be used as pre-formed compound synthesized in a separate step. The metal complex could also be used as a homogeneous species or could be attached to a solid supports either through first immobilizing the metal ion and then attaching the ligand or first by immobilizing the ligand and then coordinating the metal ion to the chelating support. As solid supports, one can use an ion exchange resin, inorganic oxide, hydroxide, zeolites, clays, polyoxometalates, carbon supports and synthetic or naturally occurring fibers. When resin is used as a solid support, the resin could, for example, be any macroporous or gel type resin. A particularly preferred resin is Dowex MSC-1. When the solid support is a clay material it could be any naturally occurring or synthetic clay. A particularly preferred clay is Montmorilonite K. Immobilization techniques include but are not limited to: (i) immobilizing the metal salt and subsequent reaction with the ligand, (ii) immobilizing the ligand and subsequent attachment of the metal salt, (iii) immobilizing the pre-formed metal-complex.

The bromine promoter according to the invention is N-bromosuccinimide, N-bromophthalimide, bromine, HBr or inorganic bromide such as NaBr, KBr or LiBr.

The term oxidant as used herein means compounds capable of either transferring active oxygen to the co-catalyst or directly oxidizing the reduced form of the TEMPO catalyst (see Scheme 1). Suitable oxidizing agents that can be employed include, but are not limited to molecular oxygen, air, hydrogen peroxide, chlorite, chlorate, bromate, hypochlorite, hypobromite, organic hydroperoxides, percarboxylic acids and the like. More particularly, the preferred oxidants are molecular oxygen and air. If oxygen or air are used, ambient pressures can be used. However, pressurized oxygen or air may have benefits in certain applications. If oxidizing agents such as hydrogen peroxide, chlorite, chlorate, bromate, hypochlorite, hypobromite, organic hydroperoxides, or percarboxylic acids are used, a molar % of from 10% to 200% may be used, based on the substrate used.

The presence of solvents in the process of the invention is needed in amount to dissolve the catalyst composition. Particularly preferred solvents include but are not limited to acetic acid, ethyl acetate, butyl acetate, acetonitrile, tetrahydrofuran, methylene chloride, chloroform, toluene, acetone, diethyl ether, methyl tert-butyl ether. Especially preferred solvent is acetic acid.

The reaction can be carried out in a relatively broad range of temperatures. When the target is the selective formation of corresponding aldehyde, the preferred temperature is in the range 40-55° C. In the instances when the acid is the desired reaction product, the preferred temperature is 55-65° C. The process of the invention can be carried out in any conventional batch, semi-batch or continuous flow reactor capable of bringing the two phases (the organic phase and the gas phase) in sufficient contact and at the same time being capable of maintaining the reaction temperature within the desired range.

In accordance with one embodiment of the present invention, the oxidation is carried out as follows:
1. Preparing a solution of TEMPO catalyst, metal salt, ligand and bromine promoter in glacial acetic acid.
2. Addition of the alcohol substrate to the catalyst solution.
3. Heating the stirred reaction solution to the desired temperature under oxygen atmosphere.
4. Monitoring the oxygen uptake and cooling the reaction after the oxygen uptake is completed.
5. Phase splitting the reaction mixture by addition of water and collecting the organic phase.

In accordance with another embodiment of the present invention, the oxidation is carried out using pre-formed metal-chelate complex and consists of the following steps:
1. Preparing a solution of TEMPO catalyst, metal-chelate and bromine promoter in glacial acetic acid.
2. Addition of the alcohol substrate to the catalyst solution.
3. Heating the stirred reaction solution to the desired temperature under oxygen atmosphere.
4. Monitoring the oxygen uptake and cooling the reaction after the oxygen uptake is completed.
5. Phase splitting the reaction mixture by addition of water and collecting the organic phase.

In the inventive processes, the TEMPO catalyst preferably is used in a concentration of 0.001-10.0% mol, more preferably about 0.1-1% mol. The metal-chelate co-catalyst preferably is used in a concentration of 0.001-10.0% mol, more preferably about 0.1-1% mol. The bromine promoter is preferably used in a concentration of 0.001-10% mol, more preferably 0.1-1%. If the molecular oxygen is the terminal oxidant, the process pressure is preferably in the range of 0-500 psi, most preferably 0-30 psi. If the desired product is 3,3-dimethyl-1-butanal (in the selective oxidation of 3,3-dimethylbutanol) the process temperature is preferably 20-80° C. and more preferably 40-50° C.

Once the reaction is completed, the crude 3,3-dimethyl-1-butanal is isolated by phase split by addition of appropriate amount of water, saturated salt solution or by extraction. The solvent used in extraction can be selected from a group of aprotic inert solvents such as methylene chloride, chloroform, ethyl acetate, butyl acetate, methyl acetate, toluene, diethyl ether, methyl tert-butyl ether, pentane, hexane, heptane. Excess solvent may be recycled after isolation of the desired aldehyde. Especially preferred solvents are methyl tert-butyl ether and ethyl acetate. The crude 3,3-dimethyl-1-butanal can be recovered in several ways, including distillation, fractional distillation, either batch or continuous, or use of a thin-film evaporator to concentrate the 3,3-dimethyl-1-butanal. The crude 3,3-dimethyl-1-butanal can also be purified as described in U.S. Pat. No. 5,905,175. A preferred purification step involves distillation at 100-106° C. and atmospheric pressure to obtain purified 3,3-dimethyl-1-butanal.

The 3,3-dimethyl-1-butanal produced by the method of this invention is suitable for the synthesis of highly pure N-[N-(3,3-dimethylbutyl)-L-α-aspartyl]-L-phenylalanine methyl ester (neotame).

The following examples are provided for illustrative purposes only; the claimed invention shall not be construed as limited to the examples set forth below.

EXAMPLE I

Comparative Example 1

Example I represents a reference oxidation reaction under the conditions analogous to the one reported by A. Cecceto, F. Fontana, F. Minisci and F. Recupero in Tetrahedron Letters, 42 (2001) 6651-6653 which is represented to be one of the most effective catalyst systems for aerobic oxidation of alcohols with molecular oxygen The oxidation reactions were run in a constant volume, constant pressure volumetric system. The glass autoclave used for these experiments was a jacketed reaction flask equipped with a thermocouple, septa fitted addition port and a Teflon coated magnetic stir bar. The reaction flask was connected to an oxygen delivery unit in which gas uptake can be automatically measured and recorded with the progress of the reaction. The reactor is alternately evacuated and purged with oxygen at least five times and the temperature of the catalyst solution was raised to the target value of 45° C. under constant stirring at 1200 RPM.

The catalyst solution was prepared by charging 51 mg of $Mn(NO_3)_2H_2O$ (0.205 mmol), 60 mg of $Co(NO_3)_2 0.6H_2O$ (0.205 mmol), 85 mg TEMPO (0.536 mmol) and 7 cc of glacial acetic acid in the jacketed glass reactor. The stirring was initiated and the thermostating liquid was run into the reactor jacket to bring the catalyst solution temperature to 45° C. When the temperature reached the target value, 8200 mg of 3,3-dimethyl-1-butanol (76.6 mmol) are injected through the septum adapter using a gas tight syringe. The stirring rate was set to 1500 RPM and at this point, monitoring of the oxygen uptake was initiated and recorded against the time. Over 300 min reaction time, no oxygen uptake was recorded showing that at this high initial loads of alcohol substrate the catalyst system is inactive. The graphical presentation of this reaction is shown in the FIG. 01, Curve 1, NS1028.

EXAMPLE II

Comparative Example 2

Example II represents a second reference oxidation reaction under the same conditions as for Example I using the second catalyst system reported in the same source, Tetrahedron Letters, 42 (2001) 6651-6653:

51.0 mg of $Mn(NO_3)_2H_2O$ (0.205 mmol), 49.5 mg of $Cu(NO_3)_2.6H_2O$ (0.205 mmol), 85 mg TEMPO (0.536 mmol) are dissolved in glacial acetic acid (7 cc) and the solution transferred into a jacketed glass reactor. The reactor is alternately evacuated and purged with oxygen at least five times and the temperature of the catalyst solution is raised to the target value of 45° C. under constant stirring of 1500 RPM. When the temperature reached 45° C., 8200 mg of 3,3-dimethyl-1-butanol (76.6 mmol) are injected through the septum adapter using a gas tight syringe. The recorded oxygen uptake rate is 0.016 mmol $O_2$/min and the GC analysis after 300 min reaction time showed traces of the desired 3,3-dimethyl-1-butanal. The graphical presentation of this reaction is also shown in the same FIG. 01, curve 2, NS1029.

The data from FIG. 1 show that under reaction conditions of higher alcohol concentrations, both catalyst systems are virtually inactive and with the reaction rates recorded this procedure becomes economically not feasible for practical applications.

EXAMPLE III

Example III illustrates the oxidation of 3,3-dimethyl-1-butanol to 3,3-dimethyl-1-butanal using the catalyst system of the current invention:

170 mg of $Fe(NO_3)_3.9H_2O$ (0.416 mmol), 66 mg 2,2'-bipyridyl (0.416 mmol), 85 mg TEMPO (0.536 mmol) and 80 mg N-bromosuccinimide (0.45 mmol) are dissolved in glacial acetic acid (7 cc) and the solution transferred into a jacketed glass reactor. The reactor is alternately evacuated and purged with oxygen at least five times and the temperature of the catalyst solution is raised to the target value of 45° C. under constant stirring of 1500 RPM. When the temperature reached 45° C., 8200 mg of 3,3-dimethyl-1-butanol (76.6 mmol) are injected through the septum adapter using a gas tight syringe. The recorded oxygen uptake rate is 0.205 mmol $O_2$/min and the GC analysis after 250 min reaction time showed 95.2% conversion of the starting alcohol and 96.2% selectivity to the desired 3,3-dimethyl-1-butanal. The graphical presentation of this reaction is also shown in the same FIG. 01, curve 3, NS1016.

EXAMPLE IV

Example IV represents the potential of the catalyst composition to be used at even higher alcohol concentration in direct comparison with Example III.

170 mg of $Fe(NO_3)_3.9H_2O$ (0.416 mmol), 66 mg 2,2'-bipyridyl (0.416 mmol), 85 mg TEMPO (0.536 mmol) and 80 mg N-bromosuccinimide (0.45 mmol) are dissolved in glacial acetic acid (7 cc) and the solution transferred into a jacketed glass reactor. The dissolution and thermostating of the catalyst solution is done as in Example III. When the temperature reached 45° C., 9840 mg of 3,3-dimethyl-1-butanol (91.9 mmol) are injected through the septum adapter using a gas tight syringe. The recorded oxygen uptake rate was 0.184 mmol $O_2$/min and the GC analysis after 420 min reaction time showed 89.2% conversion of the starting alcohol and 97.4% selectivity to the desired 3,3-dimethyl-1-butanal. The graphical presentation of this reaction is also shown in the same FIG. 01, curve 4, NS1027.

EXAMPLE V

Example V represents addition protocol in which the catalysts solution and the alcohol are charged in the reactor prior purging the reactor with oxygen and raising the temperature.

170 mg of $Fe(NO_3)_3 \cdot 9H_2O$ (0.416 mmol), 66 mg 2,2'-bipyridyl (0.416 mmol), 85 mg TEMPO (0.536 mmol), 80 mg N-bromosuccinimide (0.45 mmol) and 8200 mg of 3,3-Dimethyl-1-butanol (76.6 mmol) are dissolved in glacial acetic acid (7 cc) and the solution transferred into a jacketed glass reactor. The dissolution and thermostating of the catalyst solution is done as in Example III. When the temperature reached 45° C. the stirring rate was set to 1500 RPM and at this point, monitoring of the oxygen uptake was initiated. The recorded oxygen uptake rate was 0.220 mmol $O_2$/min and the GC analysis after 230 min reaction time showed 96.3% conversion of the starting alcohol and 98.5% selectivity to the desired 3,3-dimethyl-1-butanal. The graphical presentation of this reaction is also shown in the same FIG. 01, curve 5, NS1019.

EXAMPLE VI 170 mg of $Fe(NO_3)_3 \cdot 9H_2O$ (0.416 mmol), 66 mg 2,2'-bipyridyl (0.416 mmol), 85 mg TEMPO (0.536 mmol) and 80 mg N-bromosuccinimide (0.45 mmol) are dissolved in glacial acetic acid (7 cc) and the solution transferred into a jacketed glass reactor. The dissolution and thermostating of the catalyst solution is done as in Example III. When the temperature reached 45° C., 7830 mg of 1-hexanol (76.6 mmol) are injected through the septum adapter using a gas tight syringe. The recorded oxygen uptake rate was 0.278 mmol $O_2$/min and the GC analysis after 180 min reaction time showed 90.3% conversion of the starting alcohol and 93.1% selectivity to the desired 1-hexanal.

EXAMPLE VII 170 mg of $Fe(NO_3)_3 \cdot 9H_2O$ (0.416 mmol), 66 mg 2,2'-bipyridyl (0.416 mmol), 85 mg TEMPO (0.536 mmol) and 80 mg N-bromosuccinimide (0.45 mmol) are dissolved in glacial acetic acid (7 cc) and the solution transferred into a jacketed glass reactor. The dissolution and thermostating of the catalyst solution is done as in Example III. When the temperature reached 45° C., 8900 mg of 1-heptanol (76.6 mmol) are injected through the septum adapter using a gas tight syringe. The recorded oxygen uptake rate was 0.271 mmol $O_2$/min and the GC analysis after 180 min reaction time showed 98.5% conversion of the starting alcohol and 89.7% selectivity to the desired 1-heptanal.

EXAMPLE VIII 170 mg of $Fe(NO_3)_3 \cdot 9H_2O$ (0.416 mmol), 66 mg 2,2'-bipyridyl (0.416 mmol), 85 mg TEMPO (0.536 mmol) and 80 mg N-bromosuccinimide (0.45 mmol) are dissolved in glacial acetic acid (7 cc) and the solution transferred into a jacketed glass reactor. The dissolution and thermostating of the catalyst solution is done as in Example III. When the temperature reached 45° C., 6597 mg of 3-methyl-3-buten-1-ol (76.6 mmol) are injected through the septum adapter using a gas tight syringe. The recorded oxygen uptake rate was 0.173 mmol $O_2$/min and the GC analysis after 210 min reaction time showed 100% conversion of the starting alcohol and 95.1% selectivity to the desired 3-methyl-3-buten-1-al.

EXAMPLE IX 170 mg of $Fe(NO_3)_3 \cdot 9H_2O$ (0.416 mmol), 66 mg 2,2'-bipyridyl (0.416 mmol), 85 mg TEMPO (0.536 mmol) and 80 mg N-bromosuccinimide (0.45 mmol) are dissolved in glacial acetic acid (7 cc) and the solution transferred into a jacketed glass reactor. The dissolution and thermostating of the catalyst solution is done as in Example III. When the temperature reached 45° C., 8250 mg of benzyl alcohol (76.6 mmol) are injected through the septum adapter using a gas tight syringe. The recorded oxygen uptake rate was 0.587 mmol $O_2$/min and the GC analysis after 70 min reaction time showed 100.0% conversion of the starting alcohol and 100.0% selectivity to the desired benzylaldehyde.

What is claimed is:

1. A process for oxidizing alcohols selected from the group consisting of primary and secondary alcohols to aldehydes or ketones, said process comprising the steps of (a) forming a solution including said alcohol with (i) a first catalyst selected from the group consisting of 2,2,6,6,-tetramethylpiperidinyloxy catalysts, (ii) a second catalyst selected from the group consisting of a Fe-2,2'-bipyridyl complex and a Fe-1,10-phenanthroline complex, and (iii) a bromine promoter selected from the group of N-bromo imides, organic bromides and inorganic bromides, said alcohol acting as the substrate of said solution (b) reacting said alcohol in said solution with an oxidant to produce said aldehyde or ketone.

2. The process of claim 1 wherein the second catalyst is a Fe-2,2'-bipyridyl complex.

3. The process of claim 1 wherein the second catalyst is a Fe-1,10-phenanthroline complex.

4. The process of claim 1, wherein the second catalyst concentration is 0.01-20% mol based on the substrate.

5. The process of claim 2 where the Fe-2,2'-bipyridyl complex is immobilized on ion exchange resin.

6. The process of claim 5, where the ion exchange resin is Dowex MSC-1.

7. The process of claim 2 where the Fe-2,2'-bipyridyl is immobilized on clay material.

8. The process of claim 7, where the clay material is Montmorilonite K.

9. The process of claim 1 wherein the bromine promoter is N-bromosuccinimide.

10. The process of claim 9 where the concentration of said bromine promoter is 0.01-20% mol based on the mol % of the substrate alcohol.

11. The process of claim 1, wherein the oxidant is selected from the group consisting of molecular oxygen, air, hydrogen peroxide, chlorite, chlorate, bromate, hypochlorite, hypobromite, organic hydroperoxides, and percarboxylic acids.

12. The process of claim 1, further comprising the addition of one or more solvents to the alcohol solution.

13. The process of claim 12 wherein said solvents are selected from the group consisting of: acetic acid, ethyl acetate, butyl acetate, acetonitrile, tetrahydrofuran, methylene chloride, chloroform, toluene, acetone, diethyl ether, methyl tert-butyl ether and mixture of solvents from the group above.

14. The process of claim 13 wherein said solvent is present in an amount of from 0% to about 80% based on the volume of the substrate used.

15. The process of claim 1, wherein the oxidation is carried out in absence of a solvent.

16. The process of claim 1, wherein the reaction temperature is maintained in the range of −10° C. to 100° C.

17. The process of claim 1, wherein the reaction pressure is maintained in the range of 0 psi-500 psi.

18. The process of claim 1 comprising the additional step of purification of said aldehyde or ketone by use of purification methods selected from the group consisting of distillation, fractional distillation, either batch or continuous or a thin-film evaporator.

19. A process for the production of 3,3-dimethyl-1-butanal, consisting of the step of reacting 3,3-dimethylbutanol with an oxidant wherein said 3,3-dimethylbutanol is in a solution including a catalyst selected from the group consisting of 2,2,6,6,-tetramethylpiperidinyloxy, a co-catalyst selected from the group of $Fe^{2+}$ or $Fe^{3+}$ nitrates chelated with ligands selected from the group consisting of 2,2'-dipyridyl and 1,10-phenanthroline, a bromine promoter selected from the group of N-bromo imides or inorganic bromide.

20. The process of claim 19 wherein said oxidant selected from the group consisting of molecular oxygen, air, hydrogen peroxide, chlorite, chlorate, bromate, hypochlorite, hypobromite, organic hydroperoxides, and percarboxylic acids.

21. The process of claim 19 wherein said oxidant is selected from the group consisting of molecular oxygen and air.

22. The process of claim 19 wherein said oxidant is present in an amount of from about 10 mol % to about 200 mol % based on the substrate used.

23. The process of claim 19 further comprising the addition of one or more additional solvents to the alcohol solution.

24. The process of claim 23 wherein said solvent is selected from the group consisting of: acetic acid, ethyl acetate, butyl acetate, acetonitrile, tetrahydrofuran, methylene chloride, chloroform, toluene, acetone, diethyl ether, methyl tert-butyl ether and mixture of solvents from the group above.

25. The process of claim 19 wherein said process is carried out in the absence of a solvent.

26. The process of claim 19, wherein the reaction temperature is maintained in the range of −10° C. to 100° C.

27. The process of claim 19, wherein the reaction pressure is maintained in the range of 0 psi-500 psi.

28. The method of claim 19 comprising the additional step of purification of the crude aldehyde or ketone via distillation, fractional distillation, either batch or continuous or a thin-film evaporator.

* * * * *